United States Patent
Baseeth et al.

(10) Patent No.: US 10,717,849 B2
(45) Date of Patent: *Jul. 21, 2020

(54) DISPERSANTS HAVING BIOBASED COMPOUNDS

(71) Applicant: ARCHER DANIELS MIDLAND COMPANY, Decatur, IL (US)

(72) Inventors: Shireen S. Baseeth, Decatur, IL (US); Teodora R. Tabuena-Salyers, Decatur, IL (US); Bruce R. Sebree, Oakley, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/345,822

(22) Filed: Nov. 8, 2016

(65) Prior Publication Data

US 2017/0051163 A1   Feb. 23, 2017

Related U.S. Application Data

(63) Continuation of application No. 15/075,452, filed on Mar. 21, 2016, now Pat. No. 9,517,442, which is a continuation of application No. 14/074,984, filed on Nov. 8, 2013, now Pat. No. 9,315,652, which is a continuation of application No. PCT/US2012/037241, filed on May 10, 2012.

(60) Provisional application No. 61/484,293, filed on May 10, 2011.

(51) Int. Cl.
| | |
|---|---|
| C08K 5/521 | (2006.01) |
| B01F 17/00 | (2006.01) |
| C09D 17/00 | (2006.01) |
| C09D 7/45 | (2018.01) |
| A61Q 1/02 | (2006.01) |
| A61K 8/36 | (2006.01) |
| A61K 8/365 | (2006.01) |
| A61K 8/55 | (2006.01) |
| C09D 7/20 | (2018.01) |
| C09D 7/40 | (2018.01) |

(52) U.S. Cl.
CPC ............. *C08K 5/521* (2013.01); *A61K 8/361* (2013.01); *A61K 8/365* (2013.01); *A61K 8/553* (2013.01); *A61Q 1/02* (2013.01); *B01F 17/0021* (2013.01); *B01F 17/0092* (2013.01); *C09D 7/20* (2018.01); *C09D 7/45* (2018.01); *C09D 17/003* (2013.01); *C09D 17/004* (2013.01); *C09D 17/005* (2013.01); *C09D 17/008* (2013.01); *A61K 2800/413* (2013.01); *C09D 7/40* (2018.01)

(58) Field of Classification Search
CPC ..... C10M 2223/10; C09D 17/00; C04B 28/02
USPC ................. 508/428; 106/503, 806
See application file for complete search history.

(56) References Cited

U.S. PATENT DOCUMENTS

| | | | | |
|---|---|---|---|---|
| 7,785,468 | B2* | 8/2010 | Baseeth ................... | B09B 3/00 |
| | | | | 210/610 |
| 2010/0300694 | A1* | 12/2010 | Vonderhagen ........... | A61K 8/02 |
| | | | | 166/311 |

* cited by examiner

*Primary Examiner* — Vishal V Vasisth
(74) *Attorney, Agent, or Firm* — Andrew F. Nilles

(57) ABSTRACT

The present disclosure is directed to compositions having lecithin and an organic acid and related methods. The disclosed compositions may also include one or more co-surfactants such as anionic surfactants and/or non-ionic surfactants, and may be used as a dispersant.

18 Claims, 16 Drawing Sheets

DISPERSANTS HAVING BIOBASED COMPOUNDS

CROSS-REFERENCE TO RELATED APPLICATIONS

This application is a continuation of U.S. patent application Ser. No. 15/075,452, filed Mar. 21, 2016 now U.S. Pat. No. 9,517,442, which itself claims priority to U.S. patent application Ser. No. 14/074,984, filed Nov. 8, 2013 now U.S. Pat. No. 9,315,652, which itself claims priority to International Application No. PCT/US2012/037241, filed May 10, 2012, which itself claims priority to U.S. Provisional Application No. 61/484,293, filed May 10, 2011, each of the contents of the entirety of which are incorporated herein by this reference.

TECHNICAL FIELD

The present disclosure is directed to dispersants comprising lecithin and uses thereof. The present disclosure is also directed to methods for the preparation of such dispersants and uses of the dispersants.

BACKGROUND

Dispersants and latexes have utility in applications such as paper coatings, colors, paints, and adhesives, as well as coatings for paper, metal, and the pharmaceutical industry. Although dispersants account for only a few percent of the total composition of paints and coating formulations, the dispersants play a critical role in the performance of such paints and coating formulations. The dispersants provide color stability and maximize pigment opacity by increasing the exposed surface area of the pigment particles, thus increasing coverage while reducing costs.

Dispersion is a complex process which involves variables including the chemistries of the solvent, resin, and pigments involved. Changes in these chemistries are associated with changes in the rheology and the resultant dispersant technology. Steric and electrostatic forces can stabilize pigment dispersions and are often accomplished with anionic and nonionic surfactants and their resulting effects on the pigment surface. These surfactants are easy to use, inexpensive, and effective at low concentrations. But, anionic surfactants are pH and salt sensitive. Adsorption of non-ionic surfactants is pH and salt insensitive, but such non-ionic surfactants need to be used in large amounts to be effective.

Other dispersant technologies use hyperdispersants which have higher molecular weights than traditional, surfactant-like dispersants. One type of such hyperdispersants are polymeric dispersants which have an anchoring group in their molecule that absorbs at the surface of the pigments and a polymeric chain that provides a steric stabilization barrier around the pigment particle. Although the polymeric dispersants absorb onto the dispersed pigments, such dispersants provide little wetting and emulsifying properties. Such dispersants are attractive is some water based-formulations because less foaming often results as compared to the surfactant-like dispersants.

Phosphate esters are often used in conjunction with dispersant technologies and are considered auxiliary dispersants since such phosphate esters are not used by themselves. The phosphate esters provide assistance with stabilization through steric interactions with the pigment particles.

Apart from the abilities of wetting and dispersing, dispersants also need to stabilize the suspended particles or the suspended particles will re-agglomerate. This stabilization is critical and difficult to accomplish, but when achieved, provides a colorant with a longer shelf life, improved color, gloss, and color compatibility.

One surfactant that exhibits these desirable dispersant properties is anionic phosphate esters which have a phosphate moiety as a head group. The anionic phosphate esters are synthesized with phosphoric acid derivatives and alcohol and have some residual phosphoric acid resulting in a pH as low as two. Anionic phosphate esters are often available in free acid form. The presence of the phosphate group in a formulation for a wetting or dispersing agent enhances the gloss and color acceptance property of a pigment in paint, reduces a viscosity increase due to aging of the paint, improves surface wetting, and provides a stable dispersion.

With the growing need for more biobased additives that can replace petroleum based products based on the desire for "greener" products, a need exists for biobased products that can be used in dispersants, coatings, and latex type products where the biobased products fulfill all the desired characteristics of the petroleum based counterparts.

SUMMARY

In each of its various embodiments, the present invention fulfills these needs and discloses a biobased product that can be used as a dispersant.

In one embodiment, a composition in the form of a nano-dispersion, comprises a lecithin, an acid, and water.

In another embodiment, a dispersant composition in the form of a nano-emulsion comprises an organic solvent having a dielectric constant of between 2 and 35, lecithin, and water.

In a further embodiment, a process for producing a product in the form of a nano-dispersion comprises mixing lecithin with an organic solvent having a dielectric constant of between 2 and 35, and mixing water with the organic solvent and the lecithin.

In other embodiments, uses of the compositions of the present invention as dispersants and methods of dispersing compounds are also disclosed.

It should be understood that this disclosure is not limited to the embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures, in which.

DETAILED DESCRIPTION

Figure 1:
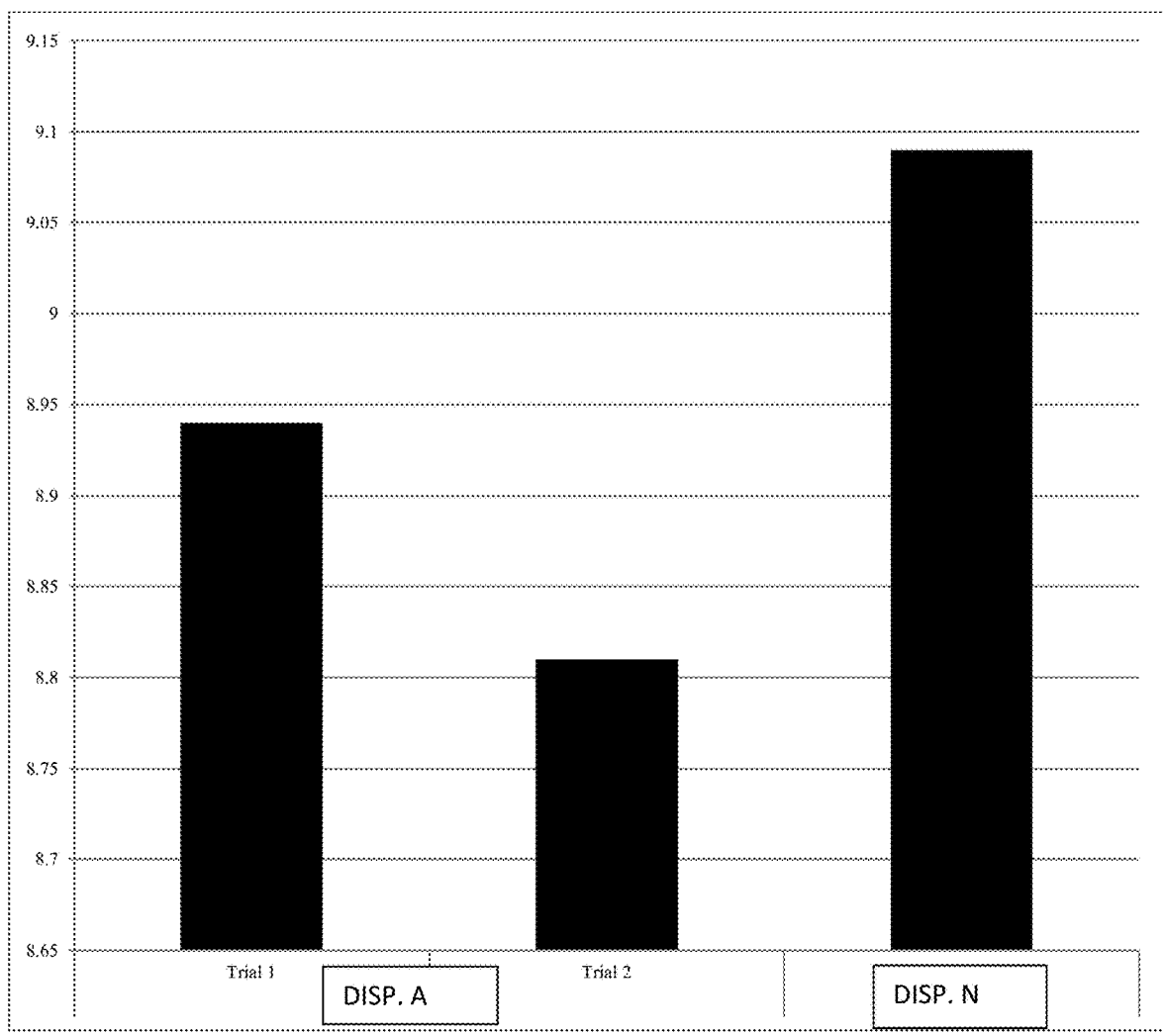
FIG. 1 shows the densities of dispersants of various embodiments of the present invention.

In the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

The embodiments disclosed herein are directed to compositions and methods that comprise a composition comprising a lecithin and an organic solvent that forms a nano-dispersion. In one embodiment, the nano-dispersions described herein self-assemble, are thermodynamically stable, and may have a mean particle size of less than one micron. In various embodiments, the composition is a blend of lecithin in amounts ranging from 5% to 95% by weight of the disclosed compositions, and in certain embodiments from 70% to 95%; and the organic solvent in amounts ranging from 5% to 95% by weight of the disclosed compositions, and in certain embodiments from 5% to 30%.

Lecithin is a lipid substance found in animal and plant tissues such as, for example, egg yolk, soybean, and canola or rapeseed. Lecithin includes various constituents including, but not limited to, phospholipids, such as, for example, phosphatidyl choline ("PC"), phosphatidyl inositol ("PI"), and phosphatidyl ethanolamine ("PE"). The amphiphilic properties of lecithin makes it an effective processing aid, emulsifier, dispersant and/or surfactant. Lecithin is also a natural ingredient than can form nanodispersions in aqueous mediums and carry high loads of actives. But, in such aqueous mediums, lecithin tends to have limited tolerance to pH and electrolytes.

Lecithin may be used in applications where modification of the boundary layer between substances is desirable. In the presence of immiscible liquid phase, lecithin can reduce the interfacial surface tension and function as an emulsifier. When used with two or more solid phases, lecithin can function as a lubricant and/or release agent.

In one embodiment, a lecithin based product of the present invention has utility in a dispersant formulation is stable at a low pH, such as down to two, and when used in an aqueous dispersion, the lecithin based product remains stable up to a pH often, and also remains stable in high amounts of silicates and electrolytes (up to 40% calcium chloride) without breaking the emulsion.

It has been found that the combination of lecithin and one or more organic solvents results in aqueous compositions having reduced viscosity as compared to conventional lecithin. The reduction in viscosity allows for increased applicability of lecithin as a dispersant in aqueous and non-aqueous systems. The disclosed lecithin-organic solvent compositions may be formulated to provide a desirable viscosity profile for numerous applications, such as, for example, pigment dispersion vehicles in paints, inks, and other coatings. In various embodiments, the disclosed lecithin-acidifier compositions have a viscosity of less than 1500 centipoise. In other embodiments, the disclosed lecithin-acidifier compositions have a viscosity of less than 1200 centipoise, less than 500 centipoise, or less than 100 centipoise.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophilic-lipophilic balance value ranging from 10.0 to 24.0, and in certain embodiments 10.0 to 18.0.

The emulsifier and/or surfactant properties of an amphiphilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No. 6,677,327, which is incorporated by reference herein in its entirety. HLB is also described in Griffin, "Classification of Surface-Active Agents by 'HLB,'" *J. Soc. Cosmetic Chemists* 1 (1949); Griffin, "Calculation of HLB Values of Non-Ionic Surfactants," *J. Soc. Cosmetic Chemists* 5 (1954); Davies, "A quantitative kinetic theory of emulsion type, I. Physical chemistry of the emulsifying agent," *Gas/Liquid and Liquid/Liquid Interfaces, Proceedings of the 2d International Congress on Surface Activity* (1957); and Schick, "Nonionic Surfactants: Physical Chemistry", Marcel Dekker, Inc., New York, N.Y., pp. 439-47 (1987), each of which is incorporated by reference herein in its entirety.

In various embodiments, the organic solvent used in the disclosed compositions and methods may be selected from the group of acidifiers consisting of a lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, salts of any thereof, esters of any thereof, or combinations of any thereof. In another embodiment, the organic solvent is selected from lactic acid, sodium lactate, ethyl lactate, or combinations of any thereof. The acidifier may also be a bio-derived acid, an organic acid, or a combination thereof. In another embodiment, a pH of the composition may be below 6, below 5, or below 4.

Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D 6866. ASTM International Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (i.e., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to be higher compared to bio-based products. In addition, companies may benefit from the marketing advantages associated with bio-derived products from renewable resources in the view of a public becoming more concerned with the supply of petrochemicals.

In various embodiments, the disclosed compositions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0.

In various embodiments, the lecithin may comprise from 5% to 95% by weight of the disclosed composition, in some embodiments from 60% to 90%, and in other embodiments from 30% to 80%; the organic solvent may comprise from 5% to 60% by weight of the disclosed composition, in some embodiments from 10% to 50%, and in other embodiments from 15% to 55%; and the water may comprise from 5% to 40% by weight of the composition, and in some embodiments from 10% to 30%.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof. In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof. In various embodiments, the surfactant comprises a non-ionic surfactant, such as, for example, a fatty acid ethoxylate.

In various embodiments, the disclosed compositions and methods may comprise lecithin, an organic solvent, and a co-surfactant, such as an anionic surfactant or a non-ionic surfactant. The organic solvent may have a dielectric constant of between 2 and 35.

The combination of lecithin and an organic solvent results in a composition having reduced viscosity as compared to conventional lecithin. The reduction in viscosity increases the applicability of the composition as a processing aid, emulsifier, dispersant and/or surfactant in various applications, such as, for example, in paints, inks, and other coating compositions. Embodiments comprising lecithin and an organic solvent find utility in aqueous systems, where the low viscosity composition is water dispersible.

In various embodiments, the disclosed water dispersible lecithin-acidifier compositions find utility in water-based coatings, including, but not limited to, latex paints. In various embodiments, the disclosed compositions may be used as dispersion vehicles for pigments in paint and ink formulations. In various embodiments, the disclosed compositions aid in pigment processing, including, but not limited to, grinding, milling and release aids, which may contribute to improved gloss, colorant, and body in pigmented formulations. The low viscosity of the disclosed compositions provides improved coating uniformity to pigments and other particulates in dispersions. Thus, the disclosed compositions provide improved dispersant, wetting agent, and/or stabilizer properties and performance.

In other embodiments, the disclosed compositions may be used in magnetic fluid applications. In one embodiment, the disclosed compositions may be used to stabilize magnetic particles in a solvent base, including, but not limited oil, a mixture of a base oil and an ester compound. The improved wetting and dispersant properties of the disclosed compositions result in reduced agglomeration of the suspended particles in magnetic fluids without resulting in adverse effects on the viscosity of the fluid.

The disclosed compositions may also be used in nanotechnology applications. In one embodiment, the disclosed compositions may be used as dispersant wetting agent, solubilizer, and/or stabilizer in nanoparticle suspensions. Additional applications for the disclosed compositions and methods include, but are not limited to, use in fiberglass, concrete, ceramics, plastics, and composites. Additional uses of the disclosed compositions include, but are not limited to, uses as textile auxiliary agents, leather finishing agents, plastic compounding agents, lubricants, oilfield drilling additives, emollients, film-formers, and mold release agents.

In addition to the multiple functionalities of the disclosed compositions as a dispersant, wetting agent, solubilizer, and/or stabilizer in various applications, the disclosed compositions also contain low or no volatile organic compounds ("VOCs"). Low VOC paints, inks, and other surface coatings may use water as a carrier instead of petroleum-based solvents. As such, the levels of harmful emissions are lower than solvent-borne surface coatings. However, dispersion of pigments and other colorants may be more difficult in aqueous-based coating systems as compared to petroleum-based systems. The disclosed compositions, therefore, may be used in low VOC coating formulations to improve pigment and colorant dispersion without contributing undesirable VOCs to the compositions.

In order to meet EPA standards, paints, inks and other surface coatings must not contain VOCs in excess of 200 grams per liter. Generally, low VOC surface coatings usually meet a 50 g/L VOC threshold. For example, paints with the Green Seal Standard (GS-11) mark are certified lower than 50 g/L (for flat sheen) or 150 g/L (for non-flat sheen). Surface coatings containing VOCs in the range of 5 g/L or less according to the EPA Reference Test Method 24 may be called "Zero VOC."

In various embodiments, the compositions disclosed herein have less than 25 grams of VOCs per liter of composition. In various embodiments, the compositions disclosed herein have VOC levels of less than 5 g/L, less than 1 g/L, or less than 0.5 g/L. In various embodiments, the compositions disclosed herein may be used as low-VOC bio-derived dispersants, wetting agents, solubilizers, and/or stabilizers.

In another embodiment, the compositions of the present invention may be food grade and include a food grade surfactant such as, for example, a polysorbate.

The embodiments disclosed herein are also directed to methods of preparing the disclosed compositions. In various embodiments, lecithin is heated to a temperature above ambient temperature, an organic solvent is added to the lecithin at the elevated temperature, and the organic solvent and lecithin are mixed together to form a lecithin-organic solvent blend. The blend is cooled to ambient temperature. The resulting blend has a viscosity lower than the lecithin ingredient alone, which may be less than 3000 cP. In various embodiments, the viscosity of the lecithin-organic solvent blend may be less than 2000 cP, less than 500 cP, or less than 100 cP. In various other embodiments, one or more co-surfactants may be added to the lecithin either before or simultaneously with one or more organic solvents. The one or more co-surfactants may alternatively be added to the blend of the lecithin and the one or more organic solvents.

The embodiments disclosed herein are also directed to methods of using the disclosed compositions. In various embodiments, the disclosed compositions are used to aid in the dispersion or wetting of an ingredient in a formulation such as, for example, concrete, ceramic, fiberglass, plastic, ink, paint, or other coating. The disclosed compositions are mixed into the formulation to disperse or wet at least one ingredient, such as, for example, a pigment. In various embodiments, the disclosed compositions comprise low-VOC bio-derived additives for use in a variety of formulations.

As described herein, the disclosed compositions are suitable for formulating solvent and water based paints, inks, and other coating systems. The amphiphilic properties of the disclosed compositions allows for their use as good wetting and stabilizing agents for organic pigments, inorganic pigments, carbon black, or titanium dioxide. The disclosed compositions are also suitable for a wide variety of pigment concentrates. In various embodiments, as illustrated herein, the disclosed compositions are added as a grinding aid in pigment dispersion processes during formulation of paints, inks and other coating systems.

In various embodiments, as illustrated herein, the disclosed compositions may function as low-VOC dispersants exhibiting low-grind viscosity, high pigment load, low foam, high color development, and fast dispersion/wetting. In various embodiments, the disclosed compositions may comprise an emulsifier blend free of alkyl phenol ethoxylates.

EXAMPLES

The following exemplary, non-limiting examples are provided to further describe the embodiments presented herein. Those having ordinary skill in the art will appreciate that variations of these Examples are possible within the scope of the invention.

Example 1

This example describes a method of making a lecithin concentrate that is water dispersible. A lecithin-cosurfactant blend was prepared by mixing: lecithin (available from Archer-Daniels-Midland Company of, Decatur, Ill.) in an amount of 73 percent by weight; tall fatty acid ethoxylate (available from Stepan, Northfield, Ill.) in an amount of 20 percent by weight; and soy fatty acid in an amount of 7 percent by weight. The components were mixed at 50° C. under constant stirring for between 30 minutes to 60 minutes, thus producing an amber, transparent lecithin-cosurfactant blend.

Example 2

The lecithin-cosurfactant blend from Example 1 was mixed in an amount of 65 percent by weight with lactic acid of 88% strength (available from Archer-Daniels-Midland Company of, Decatur, Ill.) in an amount of 35 percent by weight, at room temperature with constant stirring for thirty minutes to obtain a clear system that easily forms a stable milky dispersion in water.

Example 3

The blend from Example 1 was mixed in an amount of 65 percent by weight with ethyl lactate (available from Archer-Daniels-Midland Company of, Decatur, Ill.) in an amount of 4 percent by weight, followed by the addition of water in an amount of 7 percent by weight at room temperature with constant stirring for thirty minutes to obtain a clear system that easily forms a stable milky dispersion in water. The pH of this blend is 2.0.

Example 4

The lecithin-cosurfactant blend from Example 1 was mixed in an amount of 58 percent by weight with sodium lactate of 60% strength (available from Archer-Daniels-Midland Company of, Decatur, Ill.) in an amount of 22 percent by weight, followed by 9% lactic acid of 88% strength (available from Archer-Daniels-Midland Company of, Decatur, Ill.). To this blend, ethyl lactate (available from Archer-Daniels-Midland Company of, Decatur, Ill.) in an amount of 4 percent by weight, followed by the addition of water in an amount of 7 percent by weight at room temperature with constant stirring for thirty minutes to obtain a clear system that easily forms a stable milky dispersion in water. The pH of this blend is 4.5. The composition produced by this Example is referred to as DISP. A.

Example 5

The lecithin-cosurfactant blend from Example 1 was mixed in an amount of 56 percent by weight with sodium lactate of 60% strength (available from Archer-Daniels-Midland Company of, Decatur, Ill.) in an amount of 22 percent by weight, followed by 9% lactic acid of 88% strength (available from Archer-Daniels-Midland Company of, Decatur, Ill.). To this blend, ethyl lactate (available from Archer-Daniels-Midland Company of, Decatur, Ill.) in an amount of 4 percent by weight, followed by the addition of Tergitol L-62, a polyether polyol, nonionic surfactant having an HLB value of about 7, (available from DOW Chemical Company, Midland, Mich.) in an amount of 9 percent by weight at room temperature with constant stirring for thirty minutes to obtain a clear system that easily forms a stable milky dispersion in water. The pH of this blend is 4.5.

Example 6

The lecithin-cosurfactant blend from Example 1 was mixed in an amount of 56 percent by weight with sodium lactate of 60% strength (available from Archer-Daniels-Midland Company of, Decatur, Ill.) in an amount of 22 percent by weight, followed by 9% lactic acid of 88% strength (available from Archer-Daniels-Midland Company of, Decatur, Ill.). To this blend, ethyl lactate (available from Archer-Daniels-Midland Company of, Decatur, Ill.) in an amount of 4 percent by weight, followed by the addition of propylene glycol (available from Archer-Daniels-Midland Company of, Decatur, Ill.) in an amount of 9 percent by weight at room temperature with constant stirring for thirty minutes to obtain a clear system that easily forms a stable milky dispersion in water. The pH of this blend is at 4.5.

Example 7

This Example describes a method of making a lecithin concentrate that is water dispersible. A lecithin-cosurfactant blend was prepared by mixing: lecithin (available from Archer-Daniels-Midland Company of, Decatur, Ill.) in an amount of 73 percent by weight; a blend of Polyoxyethylene (20) monooleate, Polysorbate 80 (available from BASF, Florham, N.J.) in an amount of 20 percent by weight; and soy fatty acid in an amount of 7 percent by weight. The components were mixed at 50° C. under constant stirring for between 30 minutes to 60 minutes, thus producing an amber, transparent lecithin-cosurfactant blend.

Example 8

The lecithin-cosurfactant blend from Example 7 was mixed in an amount of 58 percent by weight with sodium lactate of 60% strength (available from Archer-Daniels-Midland Company of, Decatur, Ill.) in an amount of 22 percent by weight, followed by 9% lactic acid of 88% strength (available from Archer-Daniels-Midland Company of, Decatur, Ill.). To this blend, ethyl lactate (available from Archer-Daniels-Midland Company of, Decatur, Ill.) in an amount of 4 percent by weight, followed by the addition of water in an amount of 7 percent by weight at room temperature with constant stirring for thirty minutes to obtain a clear system that easily forms a stable milky dispersion in water. The pH of this blend is 4.5. The composition of this Example is referred to as DISP. B and is food grade.

Example 9

Pigment dispersions were prepared according to formulations shown on Table 1. The composition produced in Example 4, referred to herein as DISP. A, was compared to DISP. R (produced in accordance with Example 8 of U.S. patent application Ser. No. 12/993,282, filed Nov. 18, 2010) as a standard or reference. Pigments were ground using cowles blade and glass beads to simulate bead mill for 45 minutes at 1300 rpm. Color development was evaluated at 1% pigmentation with Sherwin-Williams Gloss blue tint base. Paint mixtures were applied on white Leneta paper and dried overnight under normal laboratory condition. Color properties were determined by Spectro-guide.

TABLE 1

Formulations of DISP. A and the reference DISP. R.

|  | DISP. A | | |
|---|---|---|---|
|  | Trial 1 | Trial 2 | DISP. R |
| Grind | | | |
| Water | 69.00 | 69.00 | 69.00 |
| DISP. R |  |  | 18.00 |
| DISP. A | 18.00 | 18.00 |  |
| Tergitol L-62 | 7.50 | 5.00 | 7.50 |
| AMP-95 | 2.25 | 2.25 | 2.25 |
| Byk 024 | 1.50 | 1.50 | 1.50 |
| Hostaperm Yellow H3G (% Pigment = 30.00%) | 45.00 | 45.00 | 45.00 |
| Add after pigment grind | | | |
| Water | 6.75 | 9.25 | 6.75 |
| Total | 150.00 | 150.00 | 150.00 |

Table 2 shows the pigment dispersion and paint film properties. Replacing DISP. R with DISP. A (Trial 1) increased the paint film gloss with a very minimal increase in color development as shown by increased color strength, but very minimal color difference ($\Delta E^*$). However, the pigment dispersion of DISP. A showed some foam development as shown by DISP. A's lower density than DISP. R. Reducing the amount of Tergitol L-62 by 33% (Trial 2) decreased the paint film gloss, and resulted in a very minimal increase in color development as shown by increased color strength, but very minimal difference in color ($\Delta E^*$). However, the pigment dispersion of Trial 2 showed more foam development as shown by Trial 2's lower density than Trial 1 and DISP. R as shown in FIG. 1.

TABLE 2

Paint film properties of DISP. A and the reference DISP. R.

|  | DISP. A | | |
|---|---|---|---|
|  | Trial 1 | Trial 2 | DISP. R |
| Dispersion Properties | | | |
| Brookfield Visco (p) | 0.446 | 0.413 | 0.467 |
| Density (#/gal) | 8.94 | 8.81 | 9.09 |
| Fineness of Grind (FOG) μ | 0 | 0 | 0 |
| Paint Film Properties | | | |
| L* = 100 (lightness) | 82.77 | 82.77 | 82.83 |
| −a* (greenness) | −18.06 | −18.60 | −18.08 |
| +b*(yellowness) | 22.14 | 22.10 | 22.13 |
| $\Delta E^*$ | 0.06 | 0.06 | Std |
| Gloss | 40.10 | 37.90 | 39.10 |
| Color Strength | 100.20 | 100.18 | 100.00% |

$\Delta E^* = \sqrt{(\Delta L)^2 + (\Delta a)^2 + (\Delta b)^2}$

Figure 2:
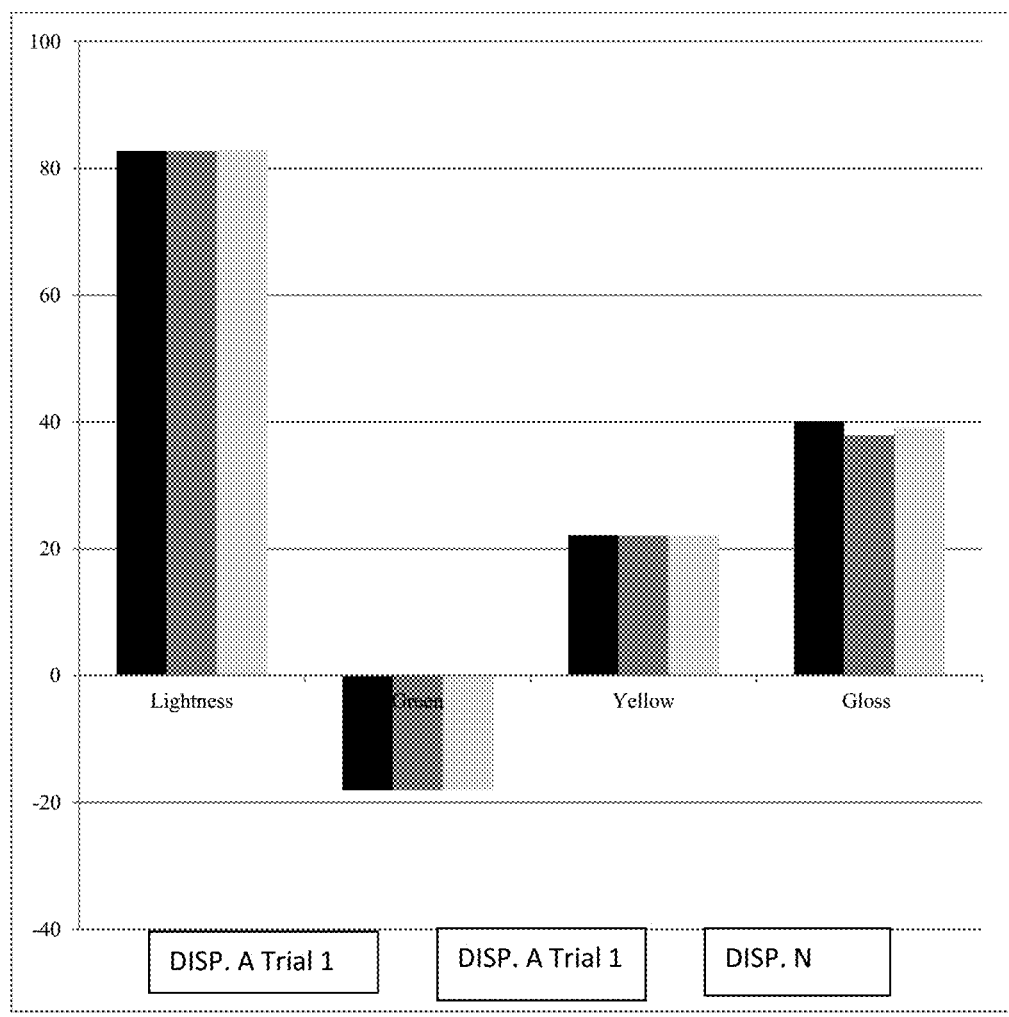
FIG. 2 is a graphical representation of properties of paint produced using an embodiment of a dispersant of the present invention.
Figure 3:
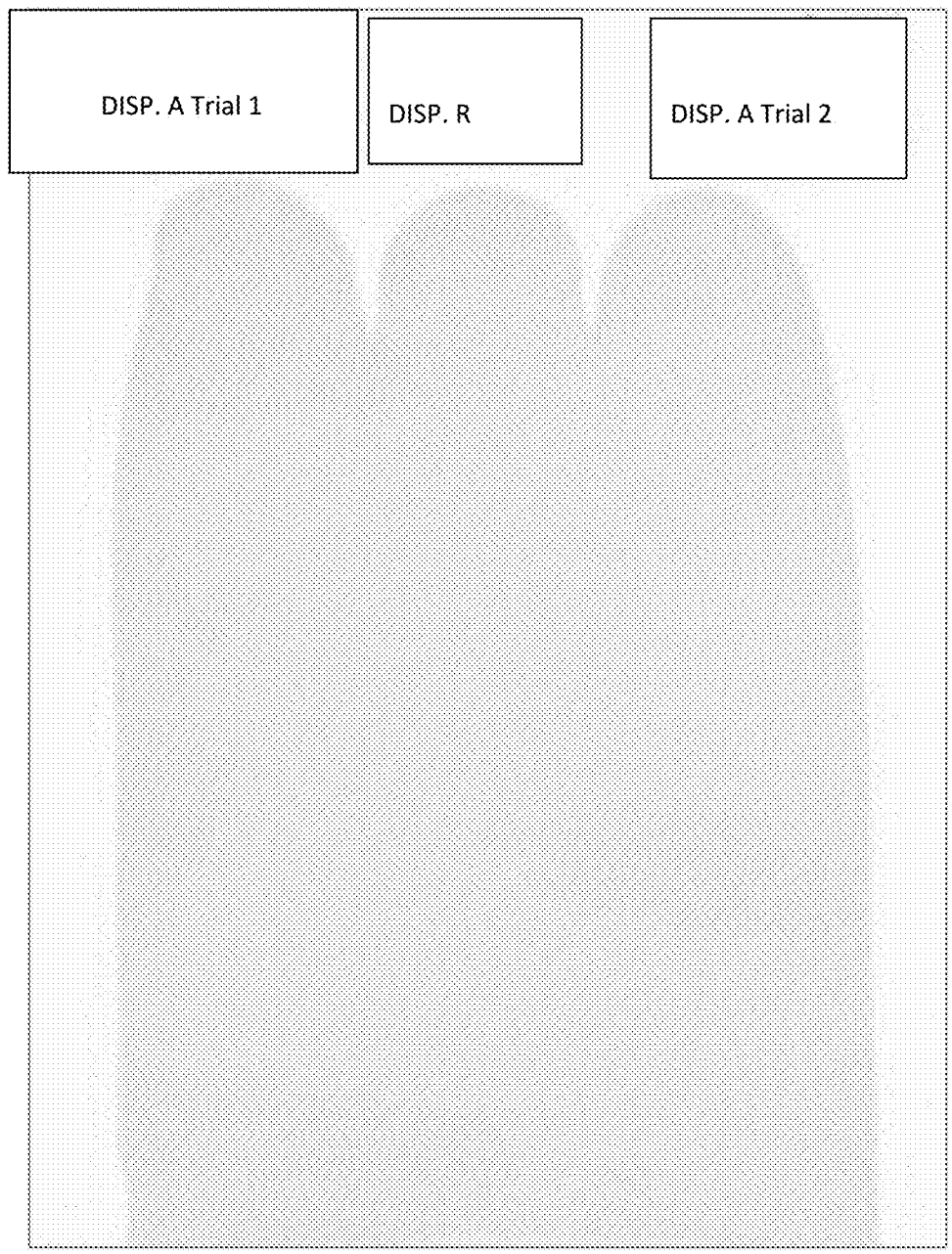
FIG. 3 shows the color of paint produced using various embodiments of dispersants of the present invention.

A graphical presentation of the paint film properties is shown in FIG. 2 and the color is shown in FIG. 3.

The DISP. A dispersant showed equal color development as DISP. R and having a little increase in gloss.

Example 10

The pigment dispersions of Example 9 (DISP. A Trials 1 and 2, and DISP. R) and the commercially available dispersant, Disperbyk from BYK, USA, were mixed with Sherwin-Williams Gloss blue tint base for color development and applied on white Leneta paper and dried overnight under laboratory conditions. Color properties were determined by Spectro-guide.

Figure 4:
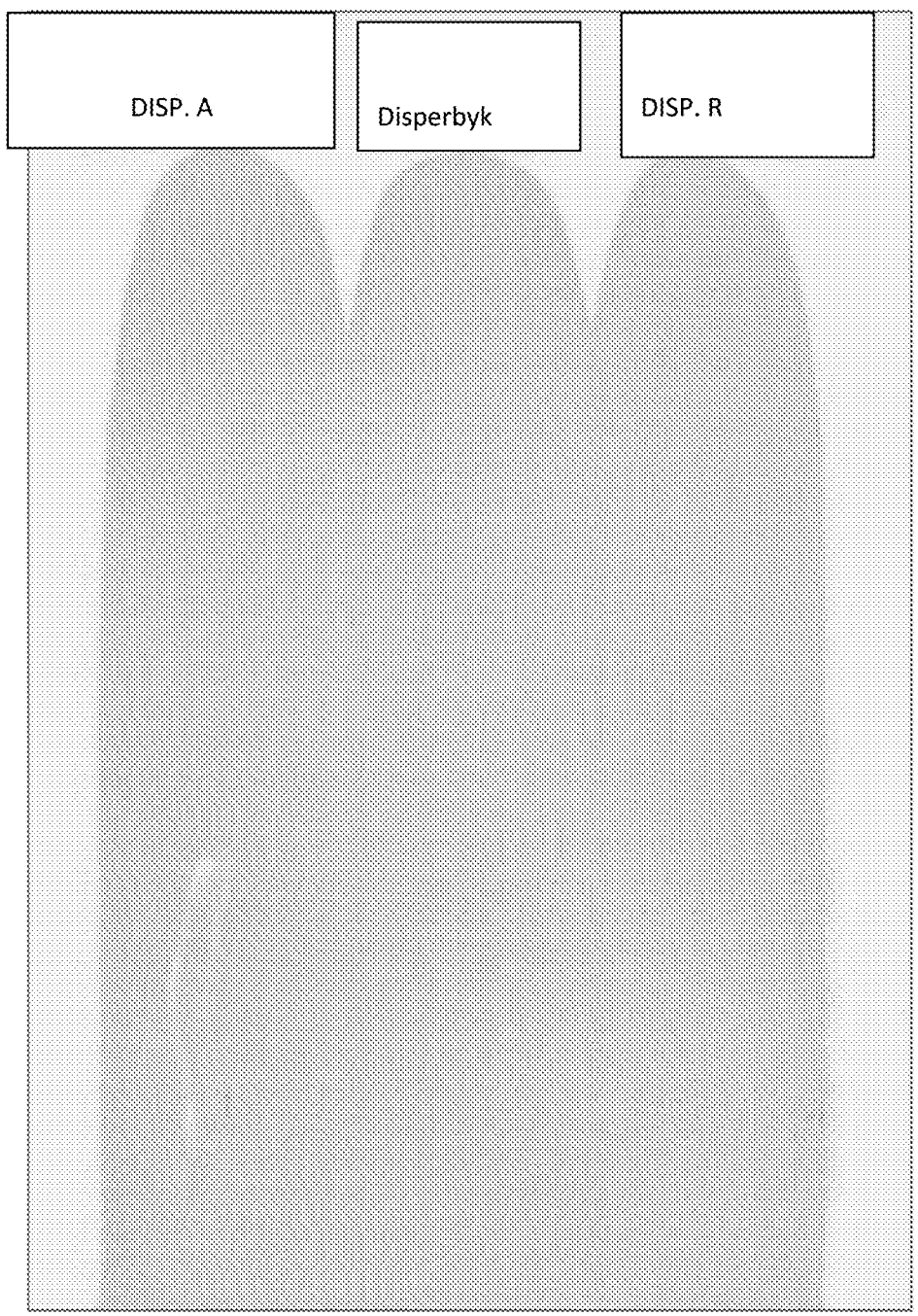
FIG. 4 shows a color comparison of a paint produced with one embodiment of a dispersant of the present invention as compared to paints produced with other dispersants.

Table 3 shows the CIELab comparison of DISP. A (Trial 1) and DISP. R with Disperbyk that were applied on the same day and the color comparisons are shown in FIG. 4. Table 4 shows the CIELab of DISP. A (Trial 1) in comparison with DISP. R and Disperbyk. From the b* values that in Tables 3 and 4, there was not much color difference between the DISP. A, DISP. R, and Disperbyk dispersants.

TABLE 3

CIELab Comparison.

|  | DISP. A Trial 1 | DISP. R | Disperbyk |
|---|---|---|---|
| L* | 82.87 | 83.02 | 82.94 |
| a* | −18.15 | −18.16 | −18.19 |
| b* | 22.25 | 22.26 | 22.38 |
| $\Delta E^*$ | 0.17 | 0.24 | Standard |

TABLE 4

CIELab Comparison.

|  | DISP. A Trial 1 | DISP. R | Disperbyk |
|---|---|---|---|
| L* | 82.57 | 82.93 | 82.91 |
| a* | −18.15 | −18.14 | −18.15 |
| b* | 22.25 | 22.34 | 22.36 |
| $\Delta E^*$ | 0.12 | 0.02 | Standard |

Example 11

Pigment dispersions were prepared according to the formulations of Table 5. DISP. A was evaluated and compared to DISP. N (produced in accordance with Example 4 of U.S. patent application Ser. No. 12/993,282, filed Nov. 18, 2010) as a standard. Pigments were ground using cowles blade and glass beads to simulate bead mill for 45 minutes at 1200 rpm. Color development was evaluated at 1% pigmentation with Sherwin-Williams Gloss White Base. Paint mixtures were applied on white Leneta paper and dried overnight under normal laboratory condition. Color properties were determined by Spectro-guide.

TABLE 5

|  | DISP. A | Standard DISP. N |
|---|---|---|
| Grind | | |
| Water | 62.10 | 62.10 |
| DISP. N | — | 18.40 |
| DISP. A | 18.40 | — |

TABLE 5-continued

|  | DISP. A | Standard DISP. N |
| --- | --- | --- |
| Tergitol L-62 | 4.60 | 9.20 |
| Dreplus L-475 | 2.30 | 2.30 |
| Bayferrox 130M (% Pigment) | 138.00 (61.22%) | 138.00 (60.00%) |
| Add after pigment grind Water | — | — |
| Total | 225.40 | 230.00 |

Figure 5:
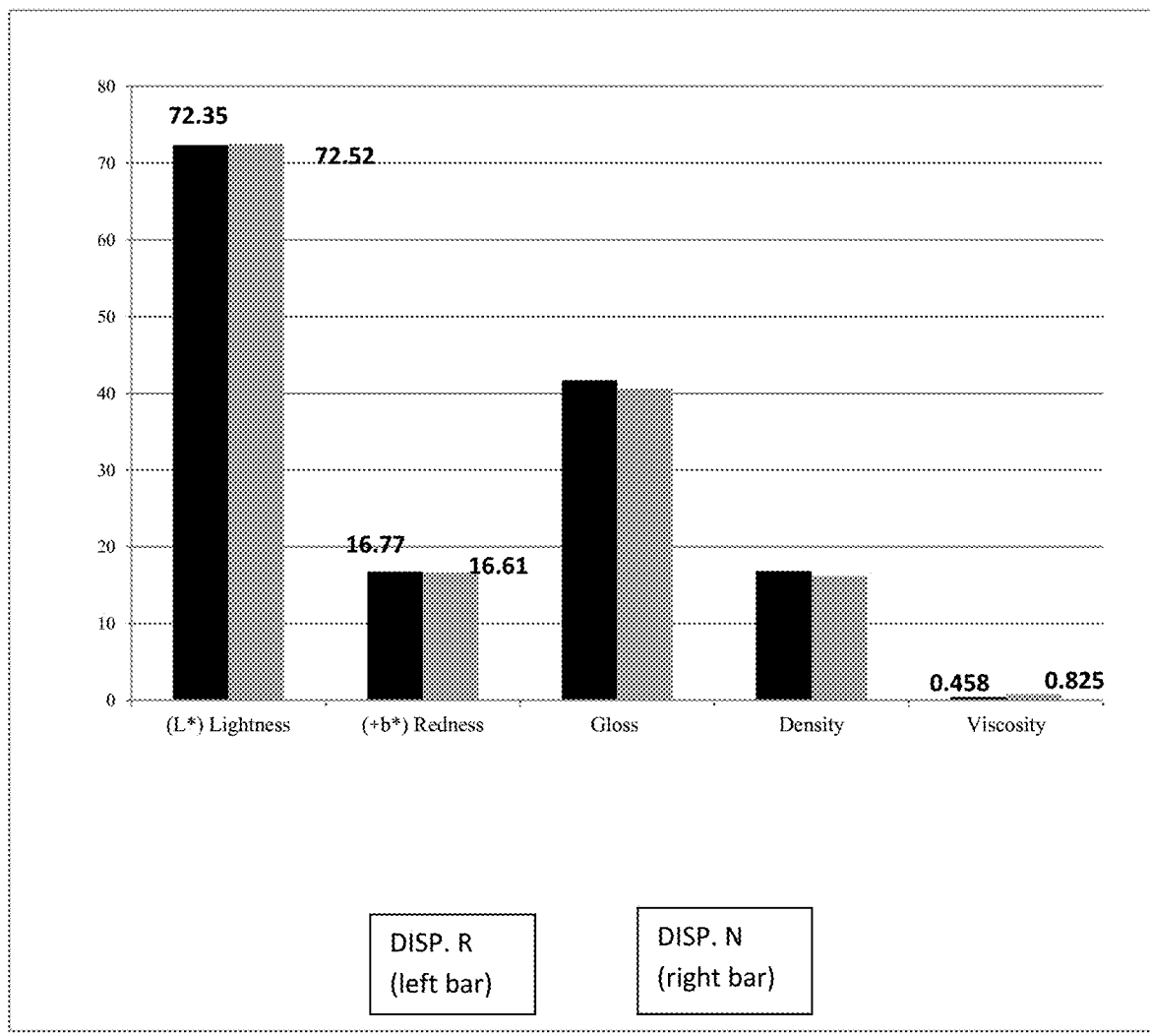
FIG. 5 is a graphical representation of properties of paint produced using an embodiment of a dispersant of the present invention.

Table 6 shows the pigment dispersion and paint film properties. Reducing the amount of Tergitol L-62 by 50% in the DISP. A formulation decreased the foam development in the dispersion as shown by its high density and low viscosity (FIG. 5). The color development for DISP. A was slightly improved as compared to DISP. N as shown by the CIELab L* and +b* values and color strength, and the gloss of the paint having DISP. A was improved as compared to DISP. N.

TABLE 6

|  | DISP. A | DISP. N |
| --- | --- | --- |
| Brookfield Visco (p) | 0.458 | 0.825 |
| Density (#/gal) | 16.85 | 16.18 |
| Fineness of Grind (FOG) μ | 10 | 10 |
| L* (=100 lighter) | 72.35 | 72.52 |
| +a* (redness) | 16.77 | 16.61 |
| +b* (yellowness) | 5.73 | 5.66 |
| ΔE* | 0.25 | Standard |
| Gloss | 41.7 | 40.6 |
| Color Strength | 100.67% | 100.00% |

Figure 6:
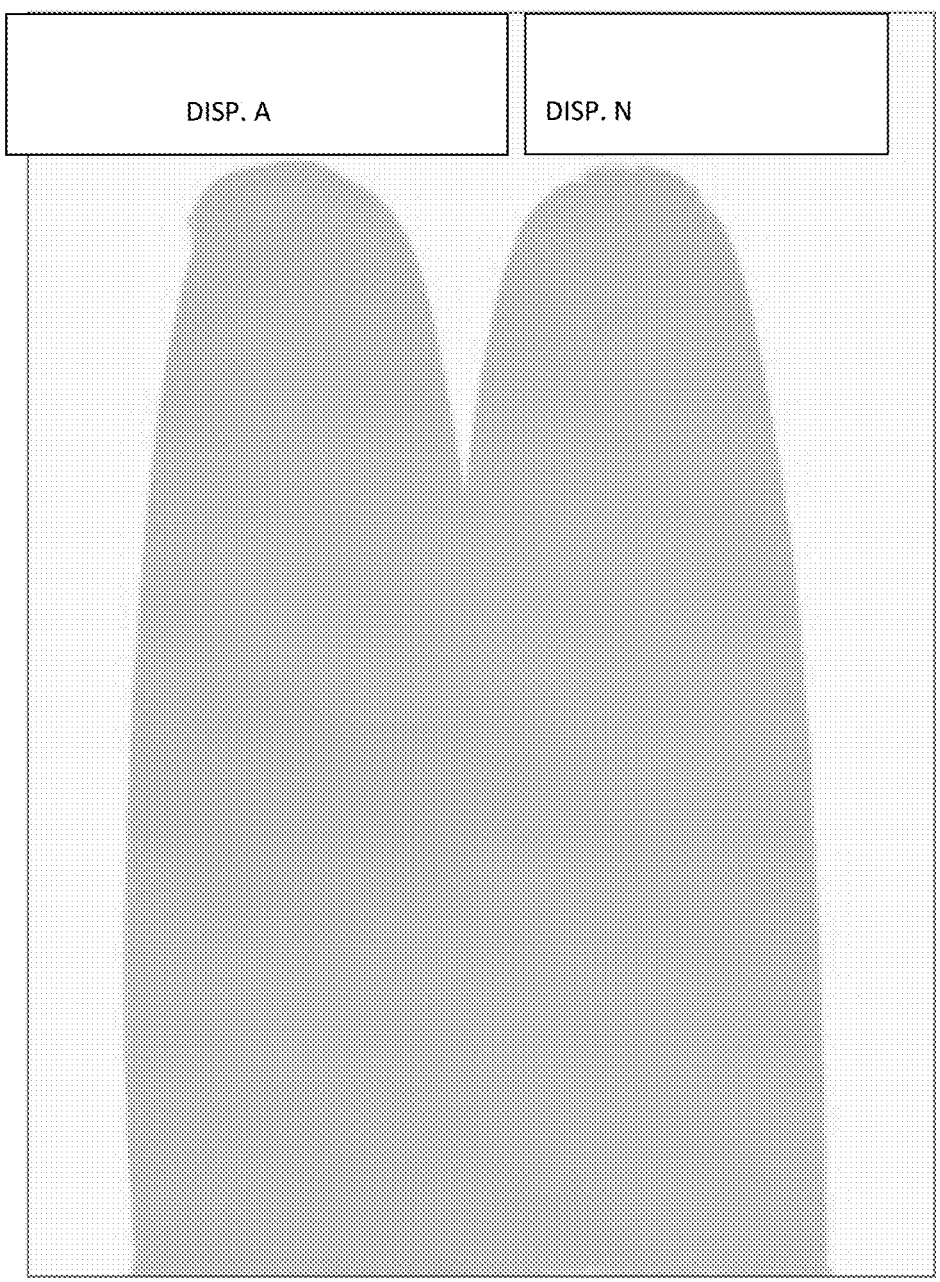
FIG. 6 shows the color of paint produced using various embodiments of dispersants of the present invention.

A graphical presentation of the paint film properties is shown in FIG. 5 and the color is shown in FIG. 6.

Example 12

Pigment dispersions were mixed with Sherwin-Williams Gloss white base for color development using DISP. A, DISP. N, Nuosperse, and Disperbyk were applied on white Leneta paper and dried overnight under laboratory condition. Color properties were determined by Spectro-guide.

Figure 7:
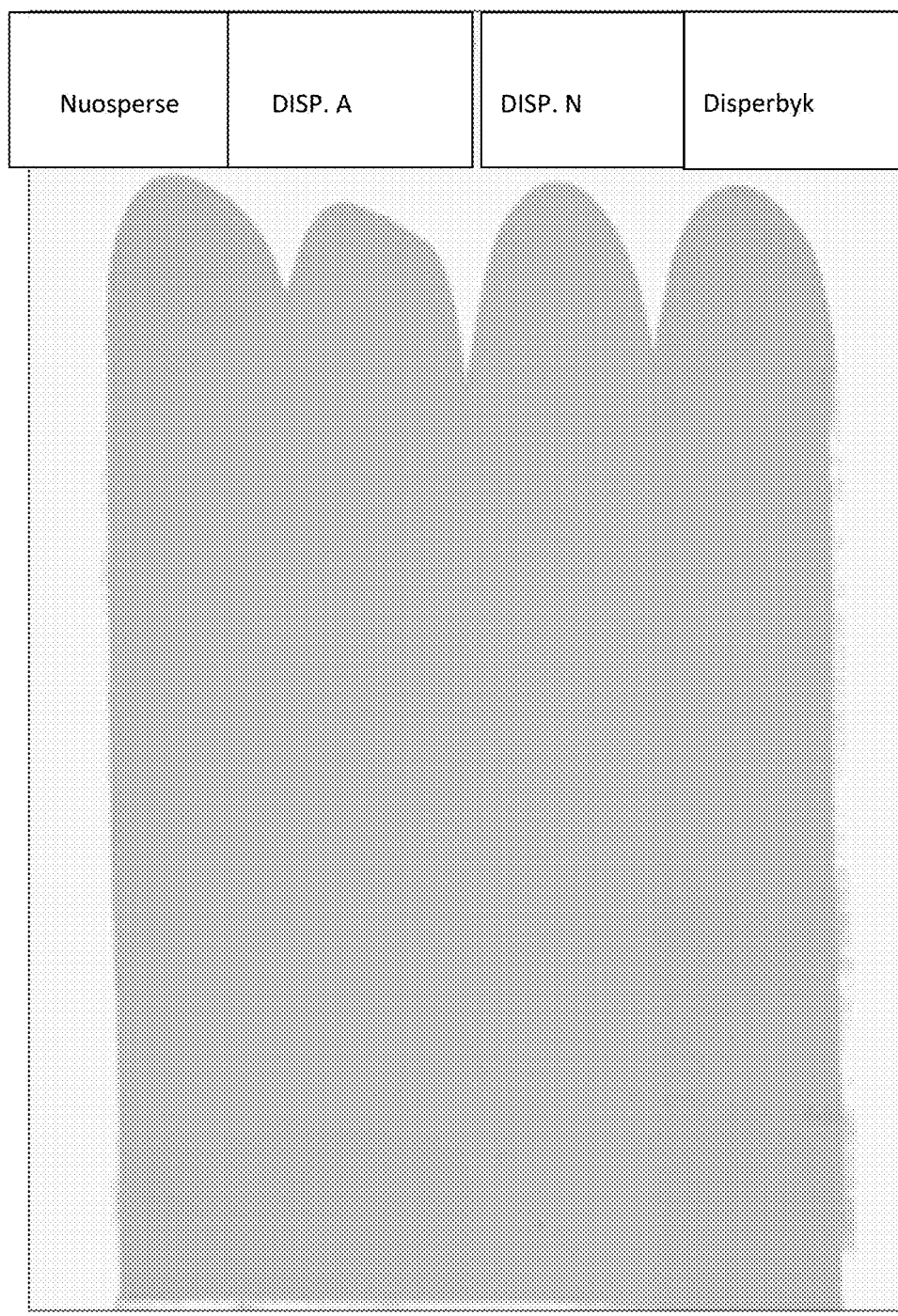
FIG. 7 shows the color of paint produced using various embodiments of dispersants of the present invention.

Table 7 shows the CIELab comparison of DISP. A and DISP. N in comparison with the commercially available dispersants Nuosperse and Disperbyk from BYK, USA, and color comparisons are shown in FIG. 7. Table 8 shows the CIELab of Lactic Blend B in comparison with DISP. N, Nuosperse, and Disperbyk. From the CIELab a* value, Lactic Blend B was comparable with Nuosperse and Disperbyk.

TABLE 7

|  | DISP. A | DISP. N | Nuosperse | Disperbyk |
| --- | --- | --- | --- | --- |
| L* | 72.24 | 72.43 | 72.08 | 71.82 |
| a* | 16.62 | 16.43 | 16.59 | 16.70 |
| b* | 5.33 | 5.57 | 5.43 | 5.52 |
| ΔE* | 0.46 | 0.69 | 0.28 | Standard |
| ΔE* | 0.17 | 0.40 | Standard | 0.28 |

TABLE 8

|  | DISP. A | DISP. N | Nuosperse | Disperbyk |
| --- | --- | --- | --- | --- |
| L* | 72.24 | 71.50 | 72.22 | 72.15 |
| a* | 16.62 | 17.31 | 16.72 | 16.70 |
| b* | 5.33 | 6.09 | 5.48 | 5.42 |
| ΔE* | 0.10 | 1.47 | 0.07 | Standard |
| ΔE* | 0.05 | 1.44 | Standard | 0.07 |

Example 13

Pigment dispersions were prepared according to the formulations of Table 9. DISP. A was evaluated with DISP. R as a standard. Pigments were ground using cowles blade and glass beads to simulate bead mill for 45 minutes at 1300 rpm. Color development was evaluated at 1.56% pigmentation with Sherwin-Williams Gloss white base. Paint mixtures were applied on white Leneta paper and color properties were determined by Spectro-guide.

TABLE 9

|  | DISP. A | Standard DISP. R |
| --- | --- | --- |
| Blend to disperse |  |  |
| Water | 69.00 | 69.00 |
| DISP. R |  | 18.00 |
| DISP. A | 18.00 |  |
| Tergitol L-62 | 7.50 | 7.50 |
| AMP-95 | 2.25 | 2.25 |
| Byk 024 | 1.50 | 1.50 |
| Hostaperm Green GNX (% Pigment = 31.41%) | 45.00 | 45.00 |
| Add after pigment dispersion Water | — | — |
| Total | 143.25 | 143.25 |

DISP. A was compared to DISP. R. 6.75 g of water was withheld in both formulations. DISP. A showed less foam development during grinding than DISP. R as shown by higher viscosity and density compared with DISP. R, and DISP. A showed an increase in gloss and comparable color development as compared to DISP. R as shown in Table 10.

TABLE 10

|  | DISP. A | Standard DISP. R |
| --- | --- | --- |
| Brookfield Visco (p) | 0.529 | 0.350 |
| Density (#/gal) | 10.17 | 9.71 |
| Fineness of Grind (FOG) μ | 0 | 0 |
| L* (=100 lightness) | 67.96 | 67.96 |
| −a* (greenness) | −43.30 | −43.69 |
| +b* (yellowness) | 1.07 | 1.00 |
| ΔE* | 0.39 | Standard |
| Gloss | 37.90 | 35.90 |
| Color Strength | 99.95 | 100.00% |

Figure 8:
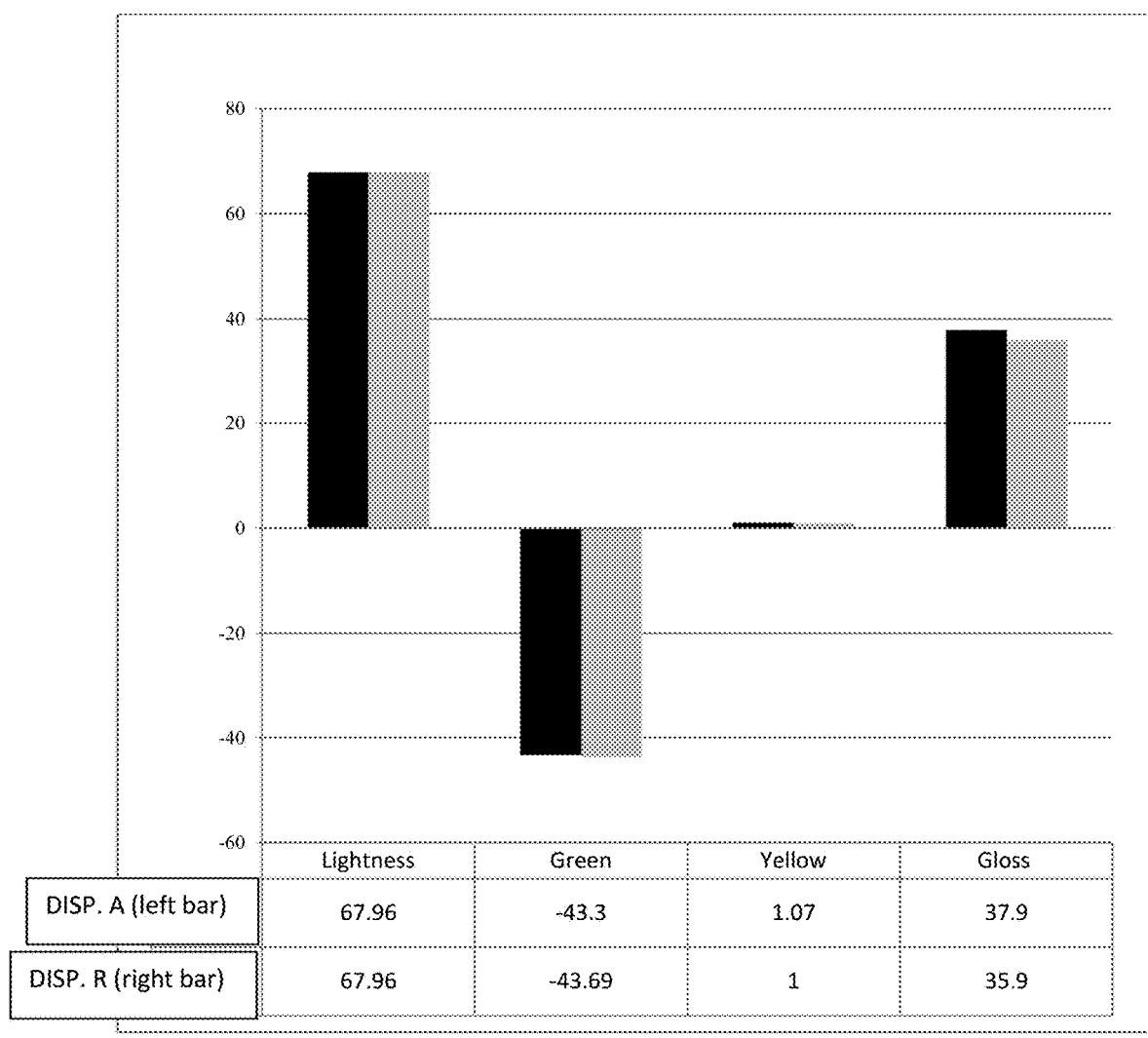
FIG. 8 is a graphical representation of properties of paint produced using an embodiment of a dispersant of the present invention.
Figure 9:
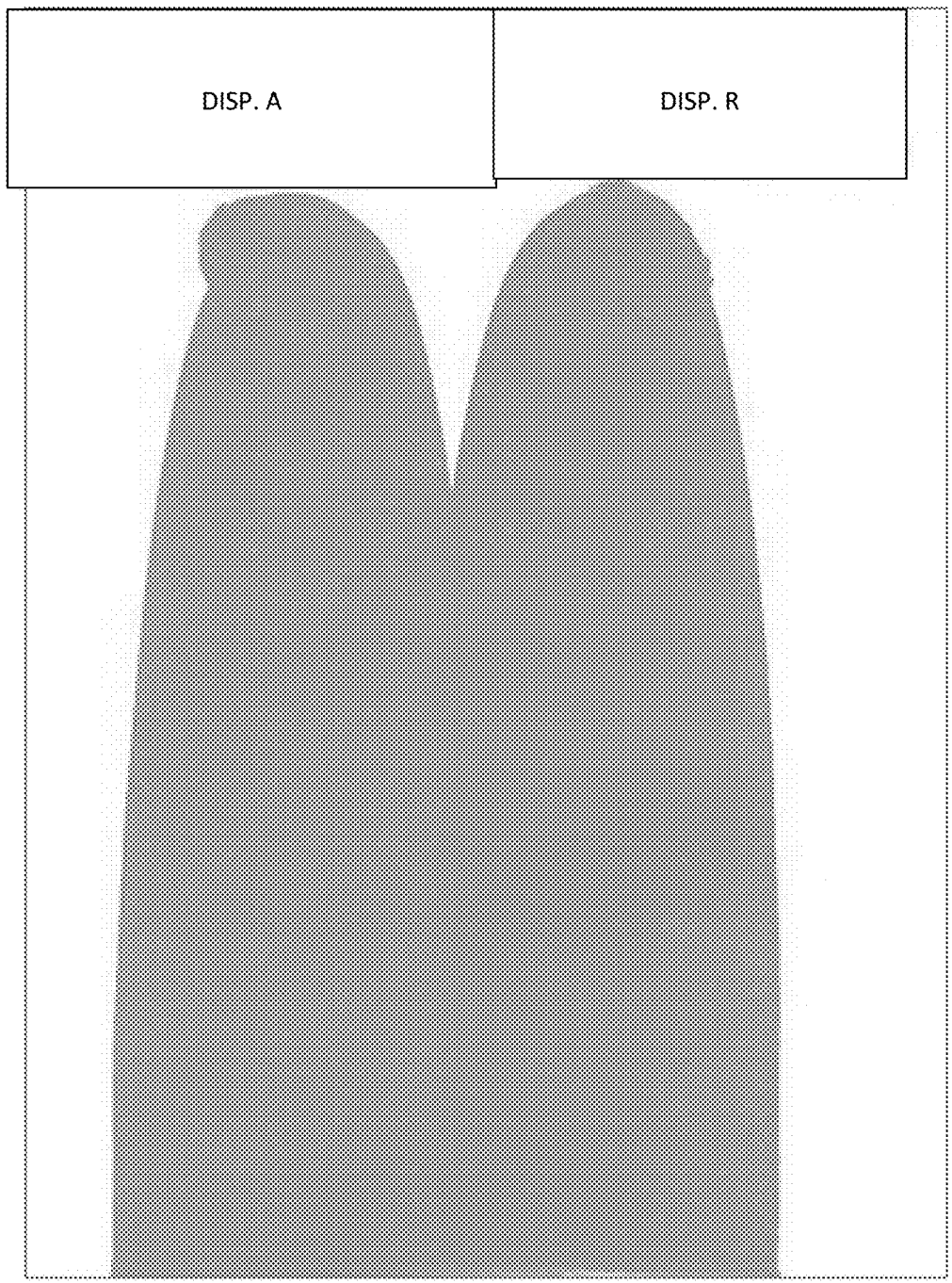
FIG. 9 shows the color of paint produced using various embodiments of dispersants of the present invention.

A graphical presentation of the paint film properties are shown in FIG. 8 and the color is shown in FIG. 9.

Example 14

Pigment dispersions that were mixed with Sherwin-Williams Extra White Gloss base for color development included DISP. A (Trial 5), DISP. R, and Disperbyk. The different pigment dispersions were applied on white Leneta paper and dried overnight under laboratory condition. Color properties were determined by Spectro-guide.

Figure 10:
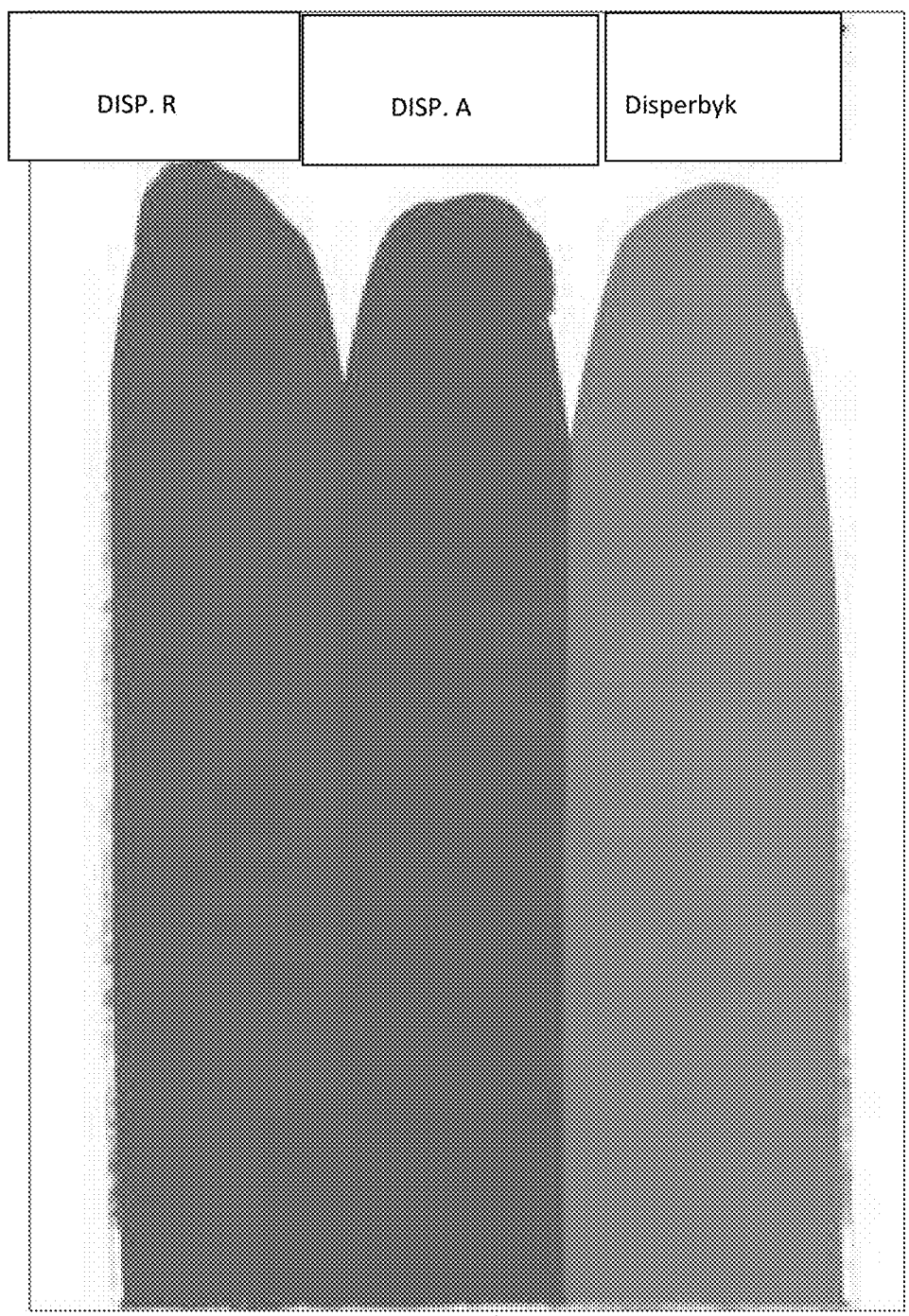
FIG. 10 shows the color of paint produced using various embodiments of dispersants of the present invention.
Figure 11:
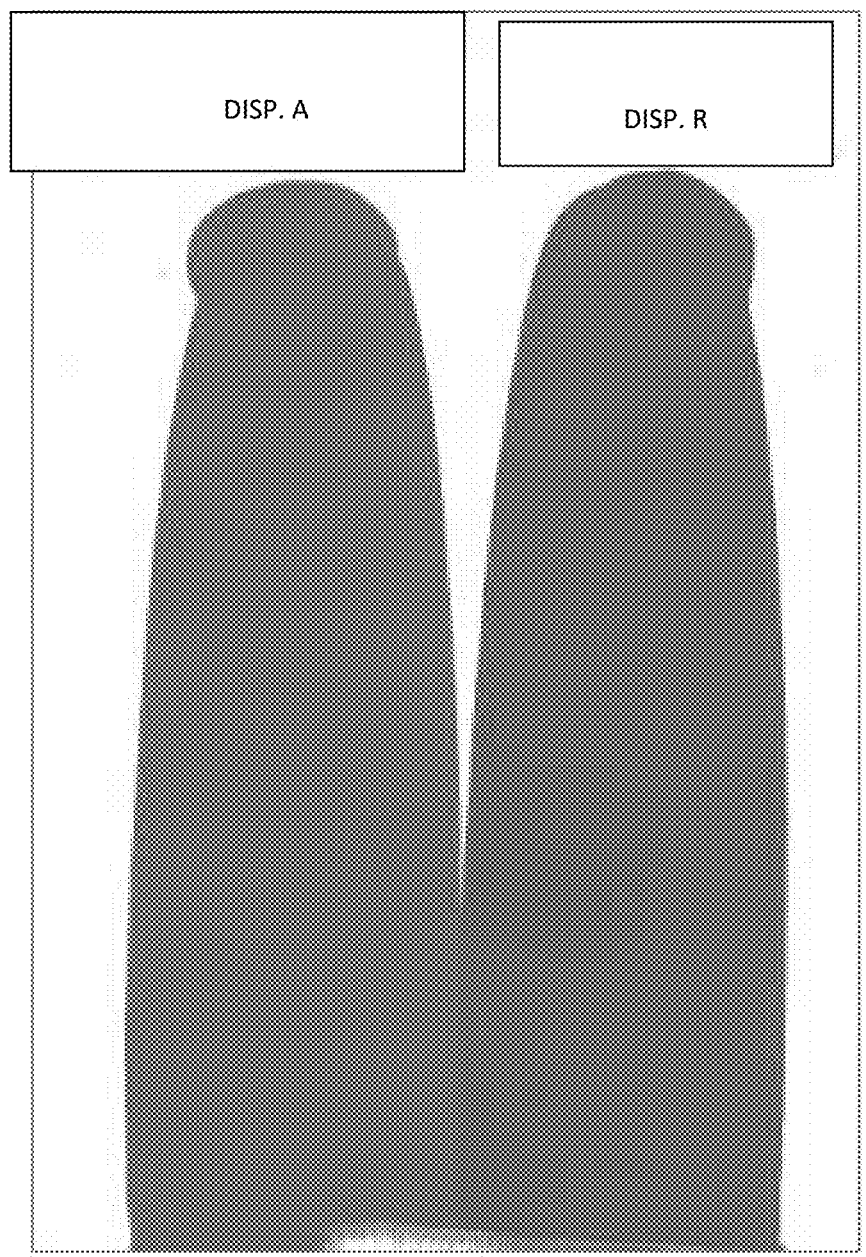
FIG. 11 shows the color of paint produced using various embodiments of dispersants of the present invention.

Table 11 shows the CIELab comparison of DISP. A, DISP. R, and Disperbyk. The color comparisons are shown in FIG. 10. Table 12 shows the CIELab comparison of DISP. A with Disperbyk and DISP. R, and color comparisons are shown in FIG. 11.

TABLE 11

|  | DISP. A Trial 5 | DISP. R | DISP. R | Disperbyk |
|---|---|---|---|---|
| L* | 43.57 | 43.83 | 43.90 | 52.27 |
| a* | −0.59 | −0.59 | −0.66 | −0.83 |
| b* | −2.59 | −2.44 | −2.58 | −2.18 |
| ΔE* | 8.93 | 8.57 | 8.56 | Standard |

TABLE 12

|  | DISP. A Trial 5 | DISP. R | Disperbyk |
|---|---|---|---|
| L* | 43.57 | 44.19 | 46.11 |
| a* | −0.59 | −0.55 | −0.65 |
| b* | −2.59 | −2.41 | −2.48 |
| ΔE* | 2.56 | 1.94 | Standard |

Figure 12:
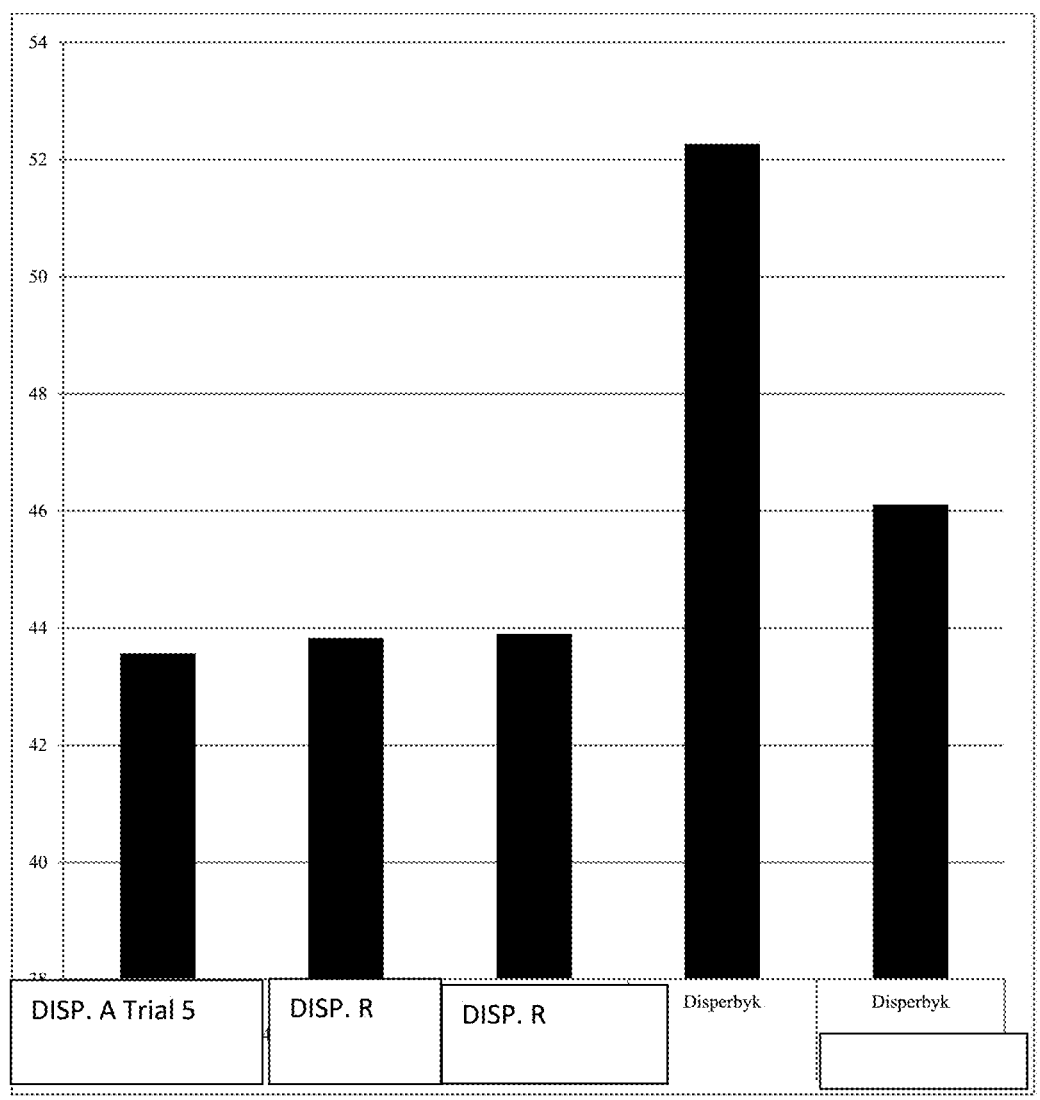
FIG. 12 is a graphical representation of properties of paint produced using an embodiment of a dispersant of the present invention.

From the CIELab L* values in Tables 11 and 12, DISP. A showed better color development than Disperbyk (the lower the value, the darker the color). Disperbyk showed color instability on storage at room temperature. This is shown on the change of color as shown in FIG. 11. FIG. 12 shows the graphical comparison of the L* values.

Example 15

Dispersion of Pigment Black

Pigment dispersions were prepared according to formulations of Table 13. Various trials were made to compare to the standard DISP. R formulation. Pigments were ground using cowles blade and glass beads to simulate bead mill for 60 minutes at 1200 rpm. Color development was evaluated at 1% pigmentation with Sherwin-Williams Gloss white base. Paint mixtures were applied on white Leneta paper and dried overnight under normal laboratory condition. Color properties were determined by Spectro-guide.

TABLE 13

Formulations of DISP. A and the reference DISP. R.

|  | DISP. A Trial 5 | DISP. R |
|---|---|---|
| Blend to disperse |  |  |
| Water | 78.00 | 78.00 |
| DISP. R | — | 17.70 |
| DISP. A | 17.70 | — |
| Tergitol L-62 | 15.00 | 15.00 |
| AMP-95 | 2.60 | 1.20 |
| Drewplus L-475 | — | 2.40 |
| Byk 021 | 1.45 |  |
| Monarch 1100 (% Pigment) | 30.00 (20.00) | 35.70 (23.80) |
| Water | 5.25 | — |
| Total | 150.00 | 150.00 |

A lb-lb substitution of DISP. R with DISP. A in the standard formulation showed an increase in viscosity during grinding, development of excess foam, and lighter color development. Several trials on reduction of Tergitol L-62 or increasing DISP. A did not decrease the foam formation and improve the color development. Replacing the defoamer Drewplus L475 with Byk 021 (Trial 4) improved the color development, however, the viscosity of the millbase increased after 60 minutes of grinding, but was still able to be filtered. Decreasing the pigmentation to about 20% (Trial 5) improved the foaming property. There was no increase in mill base viscosity in the entire 60 minutes pf grinding and color development was better than DISP. R.

Table 14 shows the dispersion and paint film properties. DISP. A (Trial 5) showed lower viscosity, better color development and higher color strength as shown by the CIELab values.

TABLE 14

Paint film properties of DISP. A and the reference DISP. R.

|  | DISP. A Trial 5 | DISP. R |
|---|---|---|
| Brookfield Visco (p) | 0.417 | 0.579 |
| Density (#/gal) | 8.93 | 8.90 |
| Fineness of Grind (FOG) μ | 5 | 5 |
| L* = 0 (darkness) | 43.42 | 43.81 |
| −a* (greenness) | −0.58 | −0.59 |
| −b*(blueness) | −2.52 | −2.37 |
| ΔE* | 0.41 | Standard |
| Gloss | 36.50 | 37.20 |
| Color Strength | 101.82 | 100.00% |

Figure 13:
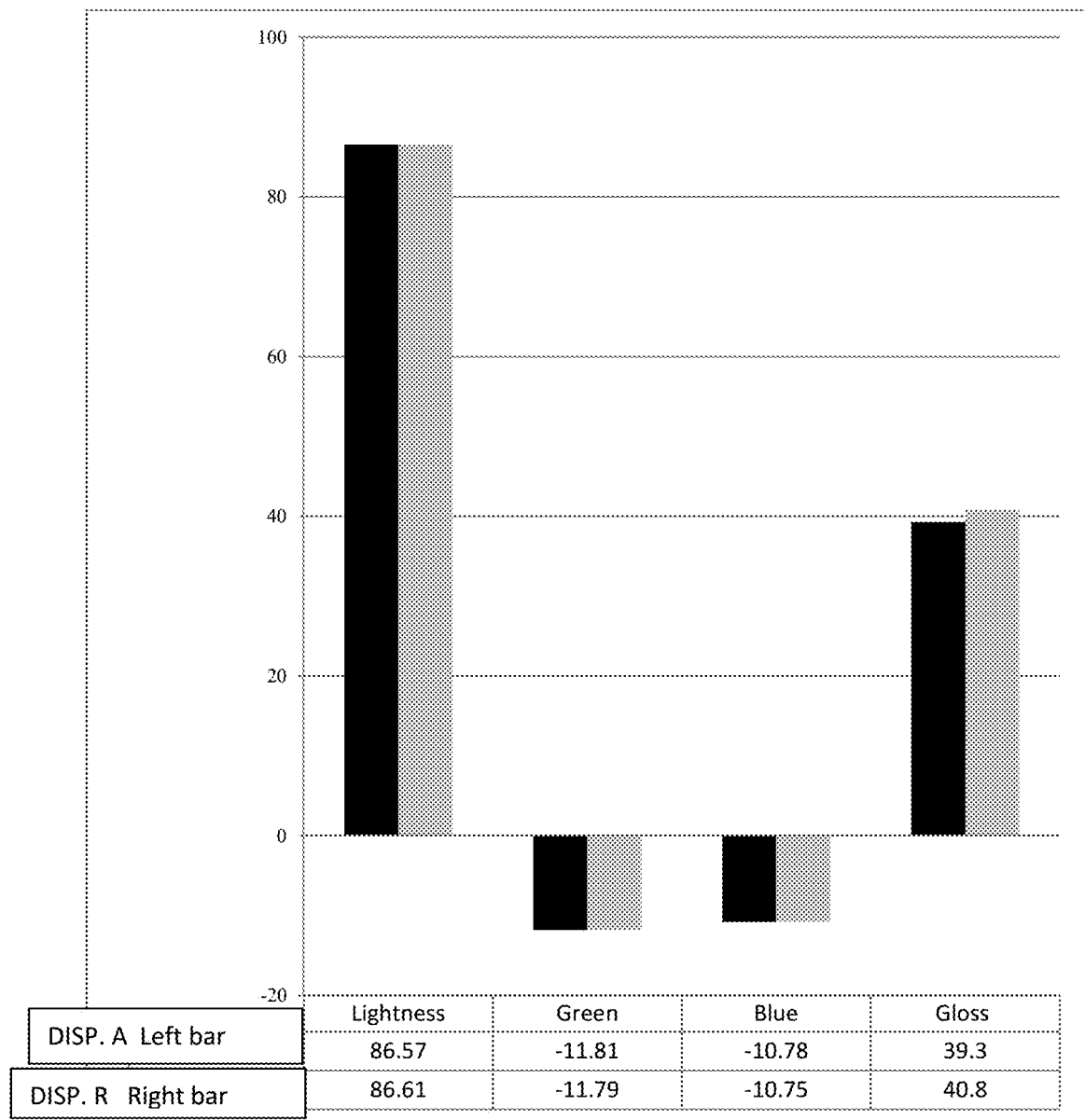
FIG. 13 is a graphical representation of properties of paint produced using an embodiment of a dispersant of the present invention.
Figure 14:
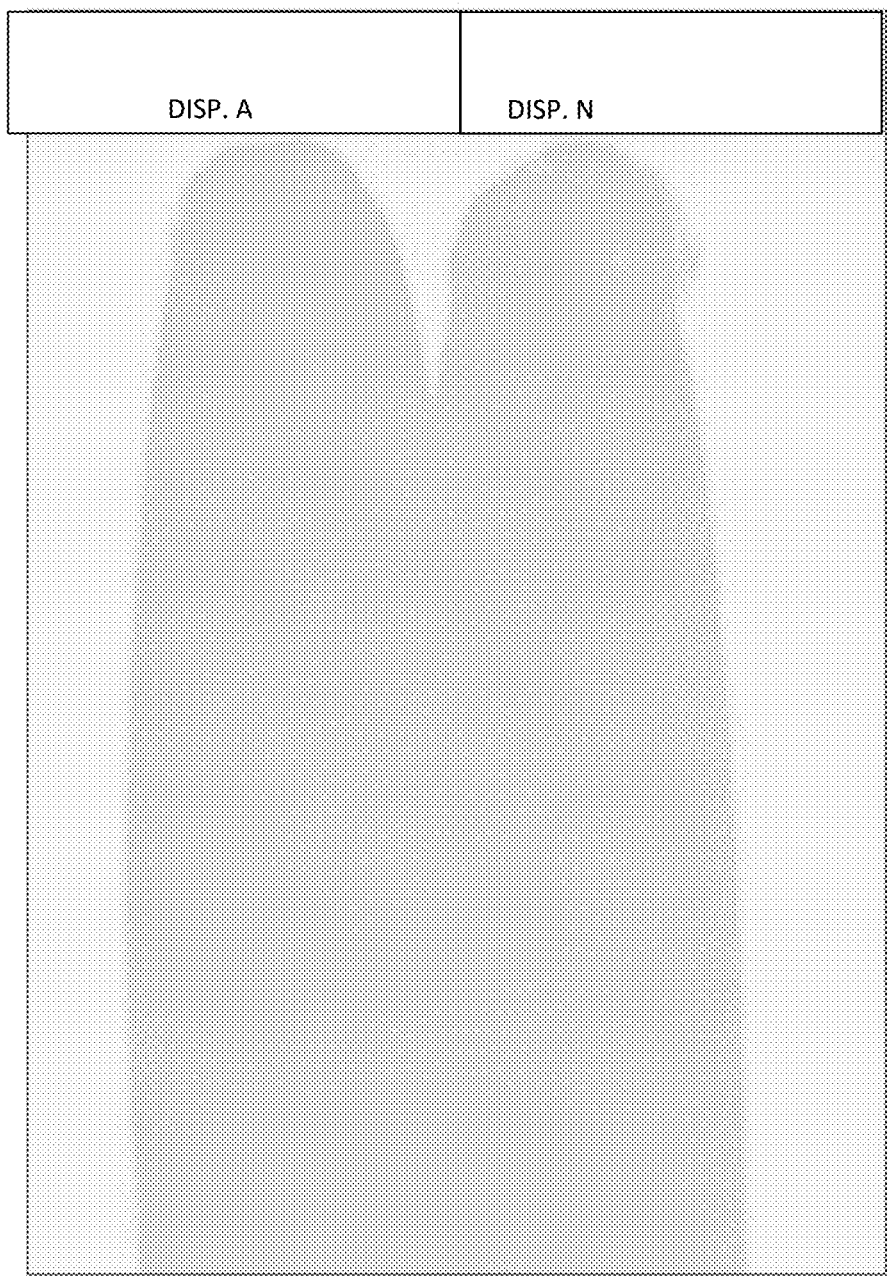
FIG. 14 shows the color of paint produced using various embodiments of dispersants of the present invention.

A graphical representation of the paint film properties is shown in FIG. 13 and color is shown in FIG. 14.

The DISP. A dispersant showed better color development than DISP. R, even at a lower pigment loading. DISP. A also improved foam development.

Example 16

Dispersion of Titanium Dioxide

Pigment dispersions were prepared according to the formulations of Table 15. DISP. A was evaluated with DISP. N as a standard. Pigments were dispersed under high speed dispersion for 45 minutes at 1600 rpm. Color development was evaluated at 1.5% in Sherwin-Williams Gloss Blue Tint Base. Paint mixtures were applied on white Leneta paper and dried overnight under normal laboratory condition. Color properties were determined by Spectro-guide.

TABLE 15

Formulations of DISP. A and the reference DISP. N.

|  | DISP. A | DISP. N |
|---|---|---|
| Blend to disperse |  |  |
| Water | 53.66 | 53.66 |
| DISP. N | — | 21.60 |
| DISP. A | 21.60 | — |
| Tergitol L-62 | 7.21 | 7.21 |
| Byk 021 | 3.60 | 3.60 |
| Titanium Dioxide R902P (% Pigment) | 252.00 (74.54%) | 252.00 (73.43%) |
| Water | — | 5.11 |
| Total | 338.07 | 343.18 |

A lb-lb substitution of DISP. N with DISP. A in the White dispersion formulation was evaluated. No additional water was added to the sample after addition of the pigment since the millbase viscosity was already low, thus increasing the pigmentation by at least 1%. Table 16 shows the dispersion and paint film properties. Both dispersants showed good dispersing property as shown by the Fineness of Grind and color development with a very minimal color difference. Pigment dispersion with DISP. A resulted in lower viscosity, slightly higher pigment loading, and minimal foam development as shown by its high density.

TABLE 16

Paint film properties of DISP. A and the reference DISP. N.

|  | DISP. A | DISP. N |
|---|---|---|
| Dispersion Properties |  |  |
| Density (#/gal) | 18.95 | 18.02 |
| Fineness of Grind (FOG) μ | 0 | 0 |
| Viscosity @ 30 rpm (cps) | 3563 | 3861 |
| Paint Film Properties |  |  |
| L* (=100 lightness) | 86.57 | 86.61 |
| −a* (greenness) | −11.81 | −11.79 |
| −b*(blueness) | −10.78 | −10.75 |
| ΔE* | 0.04 | Standard |
| Gloss | 39.30 | 40.80 |
| Color Strength | 100.11% | 100.00% |

Figure 15:
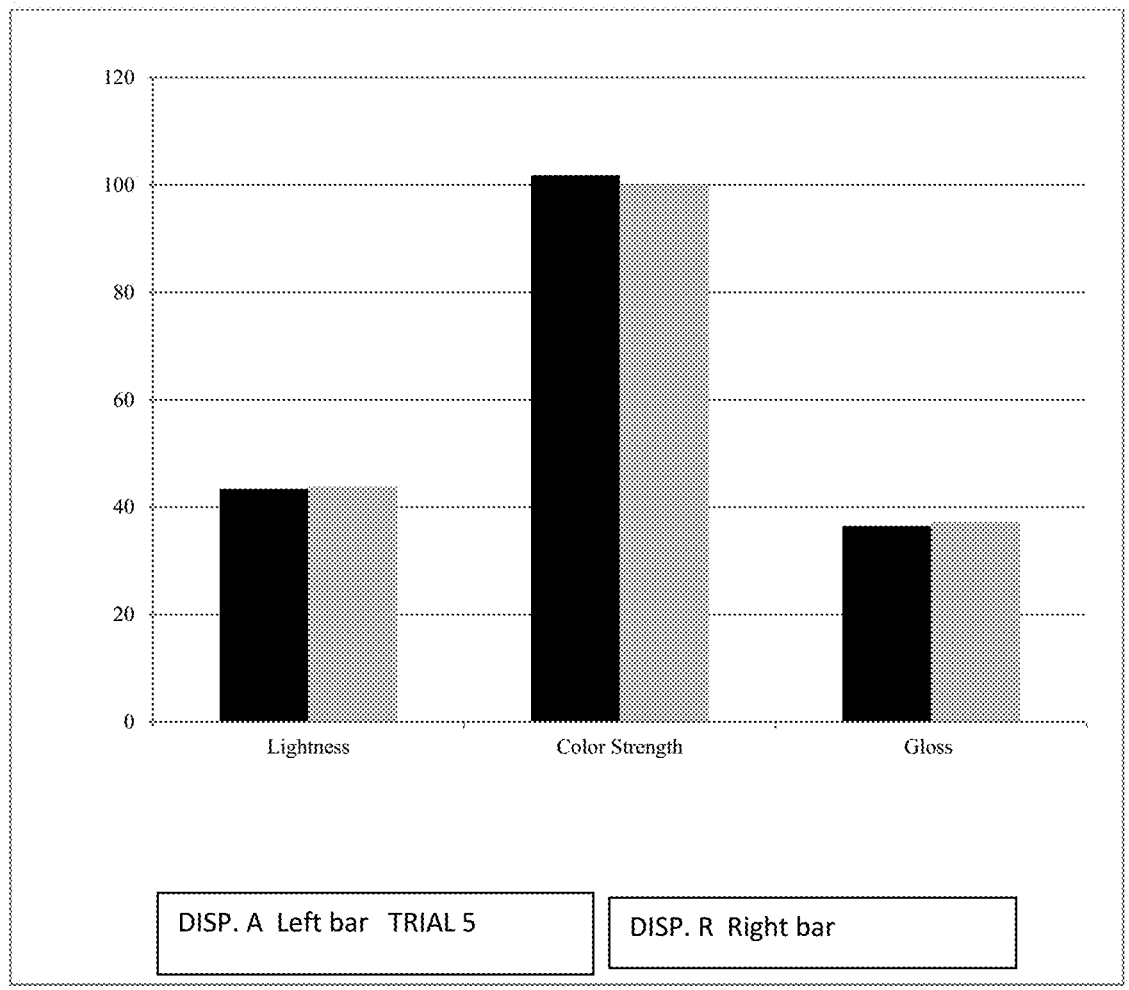
FIG. 15 is a graphical representation of properties of paint produced using an embodiment of a dispersant of the present invention.
Figure 16:
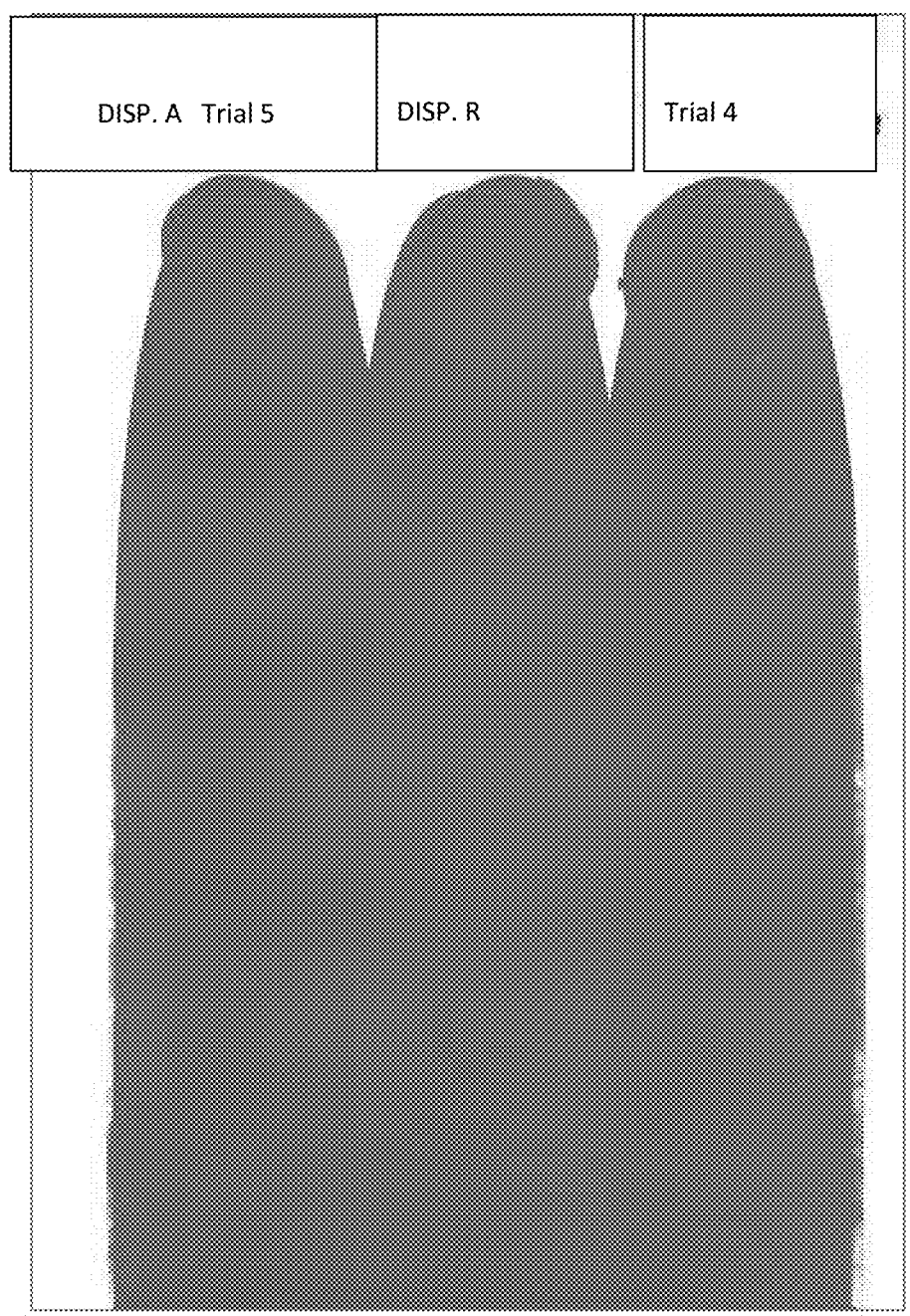
FIG. 16 shows the color of paint produced using various embodiments of dispersants of the present invention.

A graphical representation of the paint film properties is shown in FIG. 15 and color is shown in FIG. 16.

DISP. A dispersant showed equal color development with DISP. N, decreased foam development of the millibase, and increased pigment loading.

Example 17

The following Table 17 shows the effect of DISP. B being effective in increasing the pigment loading, while being able to lower viscosity and not compromising color. As shown by the Standard DISP. R, the pigment loading is very limited and an upper limit is reached with respect to viscosity. With DISP. B, a good synergy is seen with dispersing action and pigment loading where pigment loading may even reach 42%. Similar results were obtained with organic pigments.

TABLE 17

|  | DISP. B | DISP. R | DISP. R/ DISP. B |
|---|---|---|---|
| Blend to disperse |  |  |  |
| Water | 42.14 | 52.7 | 41.19 |
| DISP. R | — | 11 | 7.14 |
| DISP. B | 11.6 | — | 4.74 |
| Tergitol L-62 | 2.1 | 5.8 | 2.62 |
| AMP-95 | 1.3 | 0.75 | 1.3 |
| Byk 021 | 1.05 | 0.75 | 1.04 |
| Pigment Blue (15:3) Lansco 5576 C | 41.8 | 29 | 41.98 |
| Total | 100 | 100 | 100 |

This disclosure has been described with reference to certain exemplary embodiments, compositions and uses thereof. However, it will be recognized by those of ordinary skill in the art that various substitutions, modifications or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A composition comprising:
    a nano-dispersion comprising:
        70-95% by weight of the nano-dispersion of a lecithin or a lecithin-cosurfactant blend;
        an acid;
        an ester of the acid; and
        water;
        wherein the nano-dispersion has a particle size of less than one micron;
        wherein the nano-dispersion has a pH below 6;
    wherein the nano-dispersion has a viscosity of less than 1500 centipoise at ambient temperature;
    a defoamer; and
    a pigment, a colorant, or a combination thereof dispersed in the composition.

2. The composition of claim 1, wherein the acid is an organic acid.

3. The composition of claim 1, wherein the acid is selected from the lactic acid, ethyl lactate, sodium lactate, and combinations of any thereof.

4. The composition of claim 1, wherein the acid is selected from the group consisting of lactic acid, propionic acid, methyl acetic acid, acetic acid, fumaric acid, citric acid, ascorbic acid, gluconic acid, gluconic delta lactone acid, adipic acid, malic acid, tartaric acid, a hydroxyl acid, salts of any thereof, and combinations of any thereof.

5. The composition of claim 2, wherein the lecithin is selected from the group consisting of crude filtered lecithin, de-oiled lecithin, chemically modified lecithin, enzymatically modified lecithin, standardized lecithin, and combinations of any thereof.

6. The composition of claim 1, wherein the nano-dispersion comprises:
    the acid from 10% to 50% by weight of the nano-dispersion; and
    the water from 10% to 30% by weight of the nano-dispersion.

7. The composition of claim 1, comprising less than 25 g/L of volatile organic compounds.

8. The composition of claim 1, wherein the co-surfactant is selected from the group consisting of an anionic surfactant, a non-ionic surfactant and combinations of any thereof.

9. The composition of claim 8, wherein the surfactant has a hydrophilic-lipophilic balance of between 10.0 and 24.0.

10. The composition of claim 8, wherein the non-ionic surfactant is selected from the group consisting of sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof.

11. The composition of claim 8, wherein the anionic surfactant is selected from the group consisting of sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, fluorinated anionics, and combinations of any thereof.

12. The composition of claim 1, further comprising propylene glycol.

13. A latex paint comprising:
   a nano-emulsion comprising:
      an organic acid;
      an ester of the organic acid;
      70-95% by weight of the nano-emulsion of a lecithin or a lecithin-cosurfactant blend;
      and
      water;
      wherein the nano-emulsion has a particle size of less than one micron;
      wherein the nano-emulsion has a pH below 5;
   a pigment, a colorant, or a combination thereof; and
   a defoamer.

14. The latex paint of claim 13, wherein the organic solvent is selected from the group of acidifiers consisting of a lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, salts of any thereof, and combinations of any thereof.

15. The latex paint of claim 13, wherein the lecithin is selected from the group consisting of crude filtered lecithin, de-oiled lecithin, chemically modified lecithin, enzymatically modified lecithin, standardized lecithin, and combinations of any thereof.

16. A method of dispersing a compound in a solution, the method comprising:
   mixing lecithin with a cosurfactant at a temperature above ambient temperature, thus forming a lecithin-cosurfactant blend;
   mixing the lecithin-cosurfactant blend with an ester of acid and water, thus forming a nano-dispersion comprising 70-95% by weight of the lecithin-cosurfactant blend;
   mixing the nano-dispersion with the compound in the solution;
   wherein the nano-dispersion has a particle size of less than one micron;
   wherein the nano-dispersion has a pH of below 6;
   wherein the compound is selected from the group consisting of a magnetic particle, a pigment, a colorant, or a combination thereof.

17. The method of claim 16, wherein the nano-dispersion further comprises an organic solvent selected from the group of acidifiers consisting of a lactic acid, propionic acid, methyl acetic acid, acetic acid, fumaric acid, citric acid, ascorbic acid, gluconic acid, gluconic delta lactone acid, adipic acid, malic acid, tartaric acid, a hydroxy acid, salts of any thereof, and combinations of any thereof.

18. The method of claim 16, wherein the compound is the pigment, further comprising grinding the pigment.

* * * * *